(12) United States Patent
Nashed

(10) Patent No.: US 6,874,502 B1
(45) Date of Patent: Apr. 5, 2005

(54) BREATHING CIRCUIT DISCONNECT WARNING SYSTEM AND METHOD FOR USING A DISCONNECT SYSTEM

(76) Inventor: Ramses Nashed, 626 Boca Ciega Isle Dr., St. Pete Beach, FL (US) 33706

( * ) Notice: Subject to any disclaimer, the term of this patent is extended or adjusted under 35 U.S.C. 154(b) by 0 days.

(21) Appl. No.: 10/428,480

(22) Filed: May 2, 2003

(51) Int. Cl.[7] .................................................. A62B 9/00
(52) U.S. Cl. ............................ 128/205.23; 128/202.27; 128/912; 128/204.22; 600/532
(58) Field of Search ................................ 600/529–543; 128/200.24, 202.13, 202.22, 202.27, 204.18, 204.21, 204.22, 204.23, 205.27, 207.14–207.18, 911, 912, 203.12, 205.23; 333/24 R; 285/47; 439/1, 23, 28–33, 207, 208; 307/89, 119

(56) References Cited

U.S. PATENT DOCUMENTS

| | | | | |
|---|---|---|---|---|
| 3,654,915 A | * | 4/1972 | Sanctuary .................... | 600/495 |
| 3,796,197 A | * | 3/1974 | Locher et al. .............. | 123/357 |
| 4,796,615 A | * | 1/1989 | Bullock et al. ........ | 128/202.27 |
| 5,555,890 A | * | 9/1996 | Schaller ...................... | 600/532 |
| 6,098,617 A | * | 8/2000 | Connell ................. | 128/200.26 |
| 6,575,165 B1 | * | 6/2003 | Cook et al. ............ | 128/206.17 |
| 6,632,402 B2 | * | 10/2003 | Blazewicz et al. ............ | 422/84 |
| 6,656,127 B1 | * | 12/2003 | Ben-Oren et al. .......... | 600/532 |
| 2001/0017134 A1 | * | 8/2001 | Bahr ..................... | 128/204.18 |
| 2003/0105407 A1 | * | 6/2003 | Pearce et al. ............... | 600/532 |

* cited by examiner

Primary Examiner—Glenn K. Dawson
(74) Attorney, Agent, or Firm—Edward P. Dutkiewicz

(57) ABSTRACT

A gas circuit has an outlet and an inlet. Circuit adapters are provided. An anesthesia breathing circuit has tubular breathing circuit hoses, a Y connector and a connecting elbow. The breathing circuit has an electronically conductive system of wires and contacts to form two unconnected parallel electric circuits. An endotracheal tube has a conductive strip. A capnograph has a sampling tube coupled to the breathing circuit. The capnograph is electrically coupled to the separate electric circuits. The capnograph begins an adjustable timer when the endotracheal connector completes the electrical circuit by connecting the endotracheal tube to the breathing circuit. The timer provides for the transmission of an alarm when the circuit had been completed and no carbon dioxide was detected in the breathing hoses within a predetermined amount of time. The timer also provides for the transmission of an alarm when the circuit had been completed and had been disconnected.

9 Claims, 4 Drawing Sheets

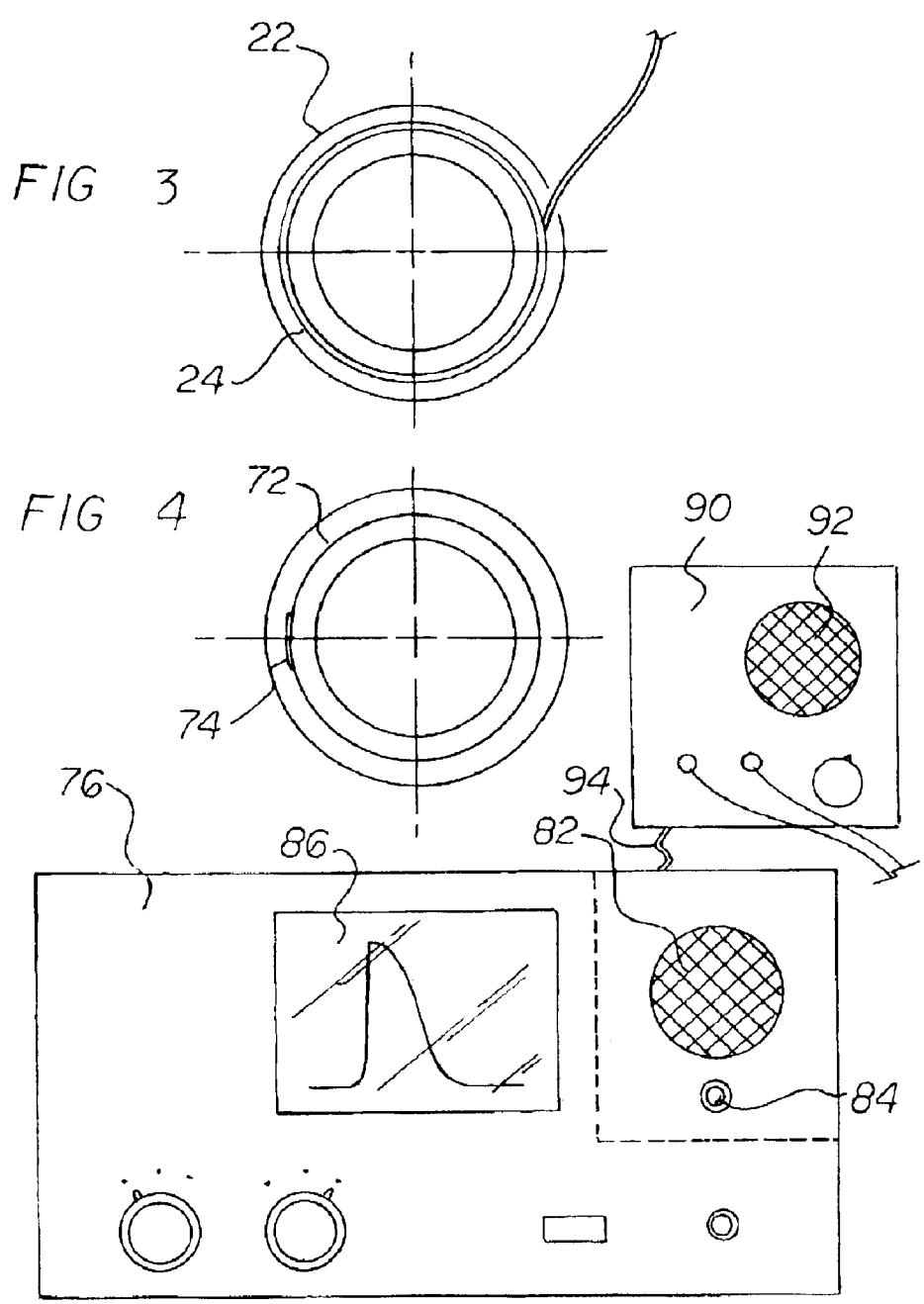

BREATHING CIRCUIT DISCONNECT WARNING SYSTEM AND METHOD FOR USING A DISCONNECT SYSTEM

BACKGROUND OF THE INVENTION

1. Field of the Invention

The present invention relates to a breathing circuit disconnect warning system and a method for using a disconnect system and more particularly pertains to allowing a user to monitor continuity within a breathing circuit.

2. Description of the Prior Art

The use of disconnect warning systems of known designs and configurations is known in the prior art. More specifically, disconnect warning systems of known designs and configurations previously devised and utilized for the purpose of warning a user of a disconnect through conventional methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 3,796,197 issued Mar. 12, 1974, to Locher et al discloses an electronic regulator with fuel injection control for diesel engines. U.S. Pat. No. 3,654,915 issued Apr. 11, 1972 to Sanctuary discloses an apparatus for automatically measuring and indicating blood pressure. U.S. Pat. No. 6,098,617 issued Aug. 8, 2000, to Connell discloses a device for administering/sampling inhalant/expired gases in an oro/nasopharyngeal airway. Lastly, U.S. Pat. No. 5,555,890 issued Sep. 17, 1996, discloses a pharyngeal end-tidal carbon dioxide measuring catheter.

While these devices fulfill their respective, particular objectives and requirements, the aforementioned patents do not describe a breathing circuit disconnect warning system and a method for using a disconnect system that allows allowing a user to monitor continuity within a breathing circuit.

In this respect, the breathing circuit disconnect warning system and a method for using a disconnect system according to the present invention substantially departs from the conventional concepts and designs of the prior art, and in doing so provides an apparatus primarily developed for the purpose of allowing a user to monitor continuity within a breathing circuit.

Therefore, it can be appreciated that there exists a continuing need for a new and improved breathing circuit disconnect warning system and a method for using a disconnect system which can be used for allowing a user to monitor continuity within a breathing circuit. In this regard, the present invention substantially fulfills this need.

SUMMARY OF THE INVENTION

In view of the disadvantages inherent in the known types of disconnect warning systems of known designs and configurations now present in the prior art, the present invention provides an improved breathing circuit disconnect warning system and a method for using a disconnect system. As such, the general purpose of the present invention, which will be described subsequently in greater detail, is to provide a new and improved breathing circuit disconnect warning system and a method for using a disconnect system which has all the advantages of the prior art and none of the disadvantages.

To attain this, the present invention essentially comprises a gas circuit. The gas circuit has an outlet with a first outer diameter. The gas circuit also has an inlet with a first outer diameter.

A first gas circuit outlet adapter is provided. The first gas circuit outlet adapter has a generally round tubular configuration. The first gas circuit outlet adapter has an inward end and an outward end. The inward end has a first inner diameter. The first inner diameter is mated to the first outer diameter of the gas circuit outlet. In this manner the coupling of the adapter to the gas circuit outlet first outer diameter is allowed. The first gas circuit outlet adapter has an outer end outer diameter. The outer end outer diameter is the same size as the gas circuit outlet outer diameter. The first adapter outlet has an electronic coupling collar. The collar is located on the outer diameter of the adapter outlet. The collar is electronically coupled to a first wire.

Next provided is a second gas circuit inlet adapter. The second gas circuit inlet adapter has a generally round tubular configuration. The second gas circuit inlet adapter has an inward end and an outward end. The inward end has a first inner diameter. The first inner diameter is mated to the first outer diameter of the gas circuit inlet. In this manner the coupling of the adapter to the gas circuit inlet is allowed. The second gas circuit inlet adapter has an outer end outer diameter. The outer end outer diameter is the same size as the gas circuit inlet outer diameter. The first adapter outlet has a second electronic coupling collar. The collar is located on the outer diameter of the adapter outlet. The collar is electronically coupled to a second wire.

An anesthesia breathing circuit subassembly is provided next. The subassembly is fabricated of a flexible material. The subassembly has a pair of tubular circuit breathing hoses. The breathing hoses have a third internal diameter. The breathing hoses have a Y connector and a connecting elbow. Each of the breathing hoses has an outward end and an inward end. A length is provided between the outward and inward ends. The inward end of each hose has an inward coupling end piece. The end piece has an outer end and an inner end. Each inward end of the end piece has a first internal diameter sized to couple with the first outer diameter of the outer adapter. The end piece of each of the breathing hoses has an electrically conductive collar. The collar is within the inner diameter of the inner end piece. In this manner the end piece mates with and forms an electronically conductive connection with the conductive collar of the gas circuit outlet adapter. The end piece collar has an electronically conductive means, such as a wire. The electronically conductive means is coupled to the end piece collar. The conductive means passes outwardly within the inner diameter of the length of the breathing hose. Each of the outward ends of the breathing hoses have an outward coupling end piece. The outward coupling end piece has an outer end. The outer end with the outward coupling end piece has a first internal diameter. The inner end of the outward coupling end piece has a third external diameter. Each outer end piece has an electronically conductive means passing from within the length of the breathing hose outwardly through to the outwardmost end of the outward end piece. The inner end of the outward end piece is coupled to the outermost end of the breathing hose.

The Y connector has a generally hollow tubular Y shaped configuration. The Y connector has two inward bifurcated portions. The Y connector has an outward common portion. Each of the bifurcated portions has a first external diameter and is sized to be accepted into the internal diameter of the outer end of the outward end piece of each of the hoses. The electronically conductive means passes through the internal diameter of the Y connector toward the outward common end. The outward common end of the Y piece has a single hollow tubular configuration. The outward common end of the Y piece has a second internal diameter. The outward common end has a pair of conductive collars. The collars are located within the second internal diameter. The collars are circumferentially parallel with a non-conductive space between the collars. Each of the electronically conductive means is coupled to one of the collars in the common end of the Y piece. The elbow has a generally hollow tubular configuration. The elbow has an inward portion and an outward portion. A capnograph connection port is provided between the inward and outward portions. The inward portion has a second external diameter. The outward portion has a second internal diameter. The inward portion has a pair of conductive collars. The collars are located on the external surface of the second external diameter. The collars are circumferentially parallel with a non-conductive space between the collars. The second internal diameter of the outward portion of the elbow has a pair of conductive collars. The collars are located within the second internal diameter. The collars are circumferentially parallel with a non-conductive space between the collars. A conductive means electronically couples the inward collar of the outward portion and the inward collar of the inward portion. A conductive means electronically couples the outward collar of the outward portion and the outward collar of the inward portion.

Provided next is an endotracheal tube connector. The endotracheal tube connector is fabricated of flexible non-conductive material. The endotracheal tube connector has a tubular portion and a coupling portion. The coupling portion has generally hollow tubular configuration. The coupling portion has a second external diameter. The tubular portion has a third external diameter. The external diameter of the coupling portion has a conductive strip. The conductive strip is aligned in an inward-to-outward direction. In this manner the conductive collars of the outward portion of the elbow are electronically coupled when the endotracheal tube connector is pushed into the second internal diameter of the elbow.

Provided last is a capnograph. The capnograph has a sampling tube. The sampling tube is coupled to the connection port of the elbow. The capnograph also has a pair of wires coupling the capnograph to the circuit adapters. The capnograph also has a program that initiates an adjustable timer when the endotracheal connector completes the circuit by connecting the collars of the outward elbow with the conductive strip. The timer provides the transmission of an alarm when the circuit had been completed and no carbon dioxide is detected in the breathing hoses within a predetermined amount of time. The program also provides the transmission of a second alarm if carbon dioxide was detected in the anesthesia circuit and the parallel monitoring circuits were not connected by the strip in the endotracheal tube. The second alarm is capable of being turned off. The program also provides a third alarm if the circuit is interrupted once it is connected and made continuous by the endotracheal tube conductive strip.

The electrical circuit formed by the coupling of the components as described above is connected to a circuit monitor which includes a timer. The circuit monitor also receives a signal from the capnograph. Once the electrical circuit is made continuous, an alarm state will be caused if no signal arrives from the capnograph within a selected amount of time, the capnograph signal being an indication of Carbon Dioxide detection by the capnograph. The lack of a capnograph signal could be cause by (1) the ventilator not being turned on after the breathing circuit was connected to the endotracheal tube (2) the capnograph not being turned on (3) no Carbon Dioxide being detected.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved breathing circuit disconnect warning system and a method for using a disconnect system which has all of the advantages of the prior art disconnect warning systems of known designs and configurations and none of the disadvantages.

It is another object of the present invention to provide a new and improved breathing circuit disconnect warning system and a method for using a disconnect system which may be easily and efficiently manufactured and marketed.

It is further an object of the present invention to provide a new and improved breathing circuit disconnect warning system and a method for using a disconnect system which is of durable and reliable constructions.

An even further object of the present invention is to provide a new and improved breathing circuit disconnect warning system and a method for using a disconnect system which is susceptible of a low cost of manufacture with regard to both materials and labor, and which accordingly is then susceptible of low prices of sale to the consuming public, thereby making such breathing circuit disconnect warning system and a method for using a disconnect system economically available to the buying public.

Even still another object of the present invention is to provide a breathing circuit disconnect warn ing sys tem and a method for using a disconnect system for allowing a user to monitor continuity within a breathing circuit thereby increasing patient safety.

Lastly, it is an object of the present invention to provide a new and improved breathing circuit disconnect warning system and a method. The system, as described above, has a gas circuit having an outlet and an inlet. Circuit adapters are provided. An anesthesia breathing circuit has tubular breathing circuit hoses, a Y connector and a connecting elbow. The breathing circuit has an electronically conductive system of wires and contacts to form two unconnected parallel electric circuits. An endotracheal tube has a conductive strip. A capnograph has a sampling tube coupled to the breathing circuit. The capnograph is electrically coupled to the separate electric circuits. The capnograph begins an adjustable timer when the endotracheal connector completes the electrical circuit by connecting the endotracheal tube to the breathing circuit. The timer provides for the transmission of an alarm when the circuit had been completed and no carbon dioxide was detected in the breathing hoses within a predetermined amount of time. The timer also provides for the transmission of an alarm when the circuit had been completed and had been disconnected.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is an end view of the inward coupling end piece taken along line 3—3 of FIG. 2.

FIG. 4 is also an end view of the coupling portion of the endotracheal tube connector taken along line 4—4 of FIG. 2.

FIG. 5 is a front view of the capnograph.

The same reference numerals refer to the same parts throughout the various figures.

DESCRIPTION OF THE PREFERRED EMBODIMENT

Figure 1:
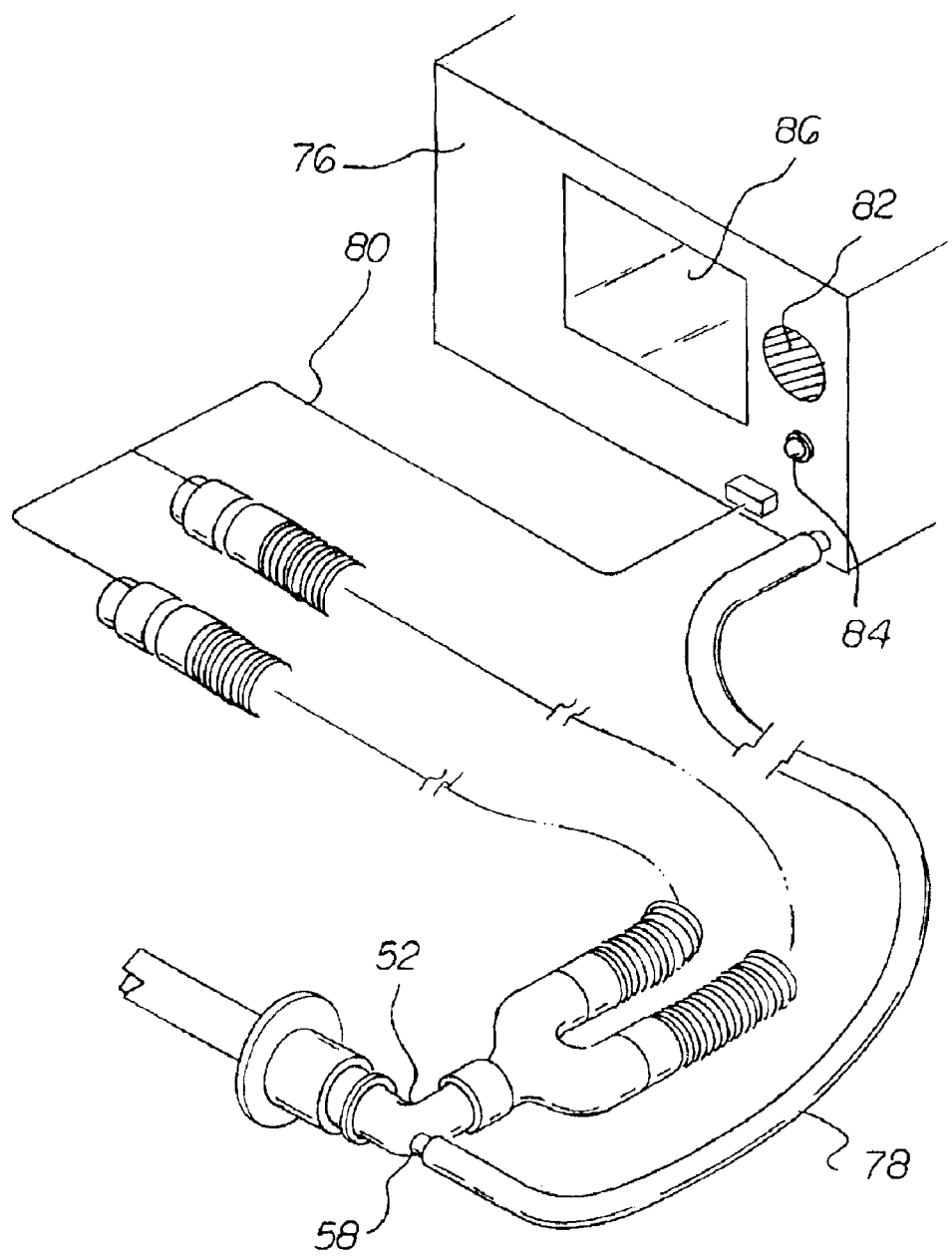
FIG. 1 is a perspective illustration of the breathing circuit disconnect warning system constructed in accordance with the principles of the present invention.
Figure 2:
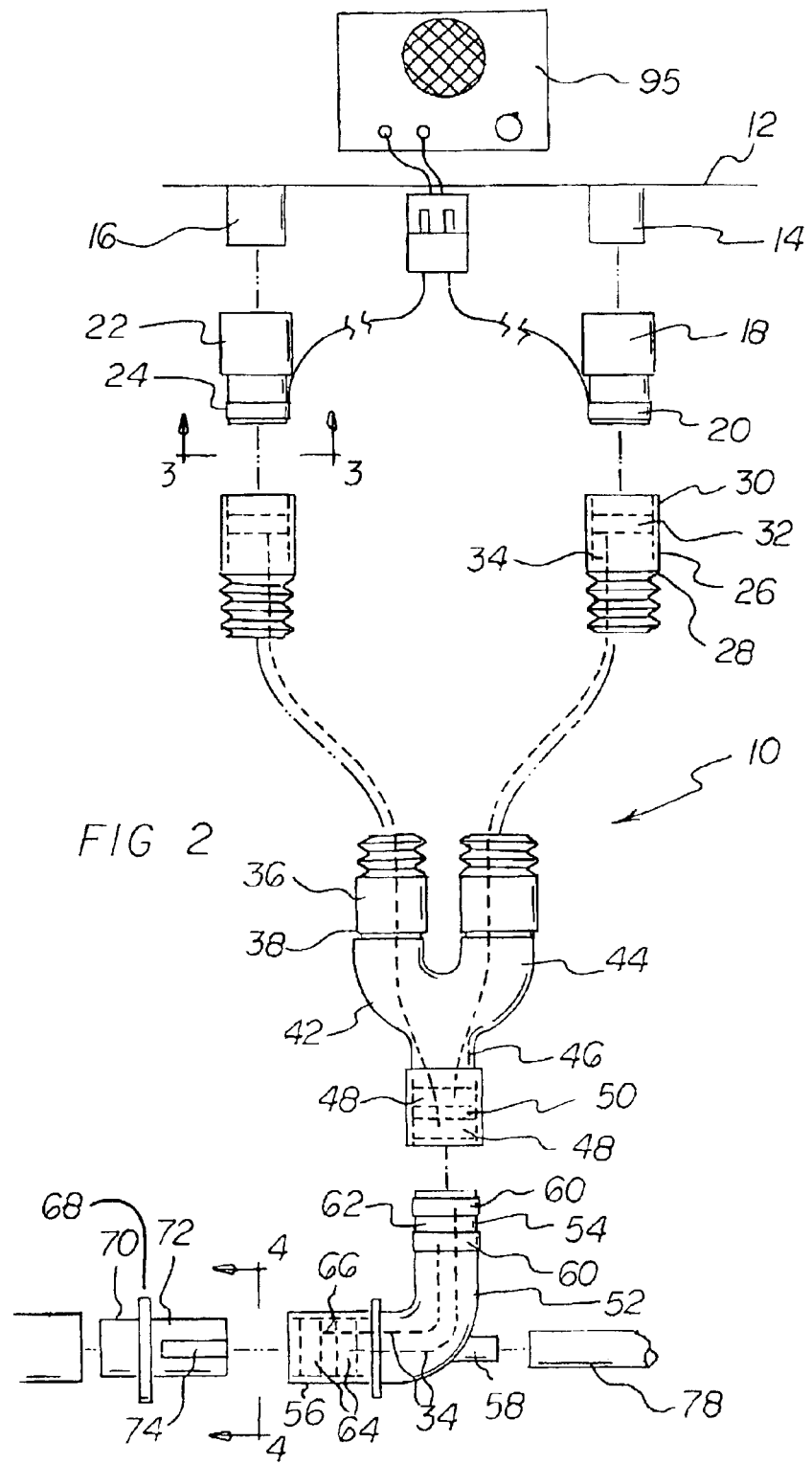
FIG. 2 is a plan view of the present invention shown in an exploded fashion.
Figure 2A:
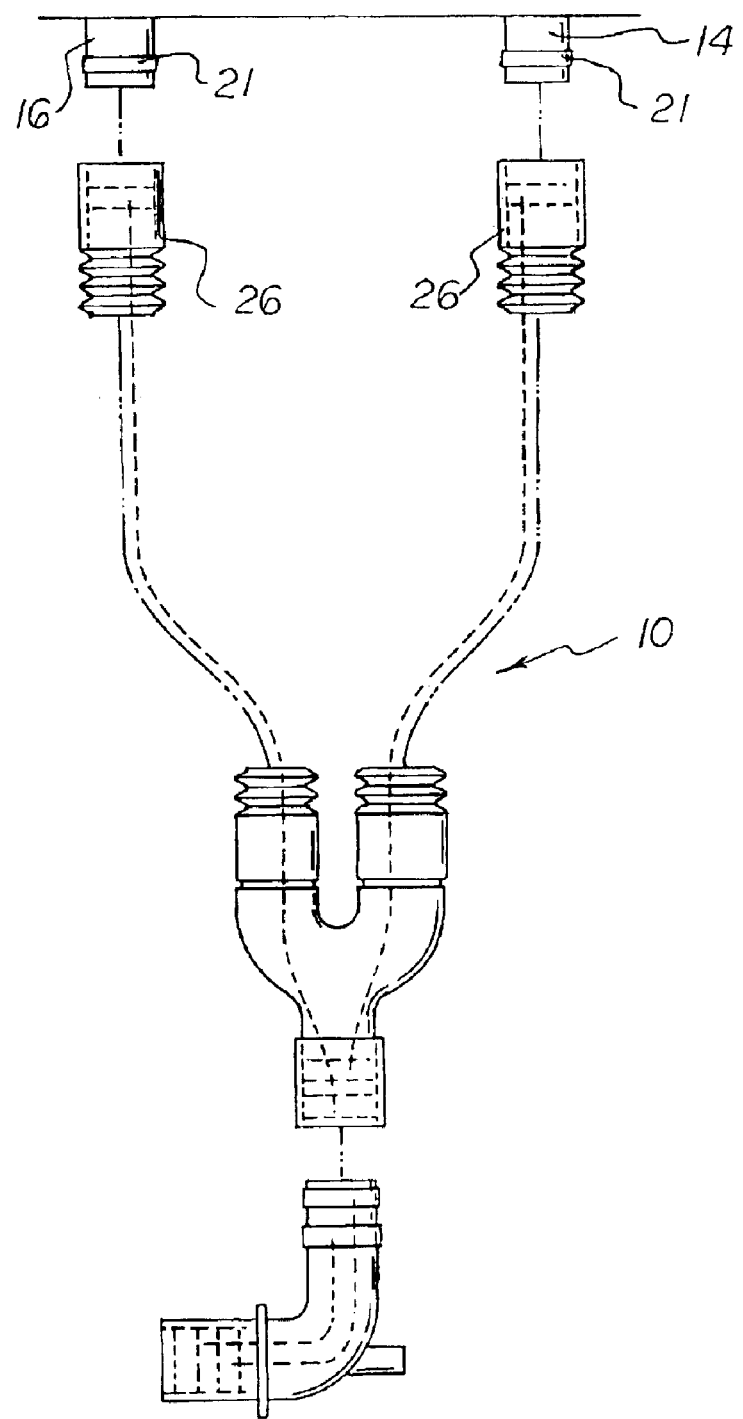

With reference now to the drawings, and in particular to FIG. 1 thereof, the preferred embodiment of the new and improved breathing circuit disconnect warning system and a method for using a disconnect system embodying the principles and concepts of the present invention and generally designated by the reference numeral 10 will be described.

The present invention, the breathing circuit disconnect warning system and a method for using a disconnect system 10 is comprised of a plurality of components. Such components in their broadest context include a gas circuit, a plurality of circuit adapters, an anesthesia breathing circuit, and an endotracheal tube. Such components are individually configured and correlated with respect to each other so as to attain the desired objective.

First provided is a gas circuit 12. The gas circuit has an outlet 14 with a first outer diameter. The gas circuit also has an inlet 16 with a first outer diameter.

A first gas circuit outlet adapter 18 is provided. The first gas circuit outlet adapter has a generally round tubular configuration. The first gas circuit outlet adapter has an inward end and an outward end. The inward end has a first inner diameter. The first inner diameter is mated to the first outer diameter of the gas circuit outlet. In this manner the coupling of the adapter to the gas circuit outlet first outer diameter is allowed. The first gas circuit outlet adapter has an outer end outer diameter. The outer end outer diameter is the same size as the gas circuit outlet outer diameter. The first adapter outlet has an electronic coupling collar 20. The collar is located on the outer diameter of the adapter outlet. The collar is electronically coupled to a first wire.

Next provided is a second gas circuit inlet adapter 22. The second gas circuit inlet adapter has a generally round tubular configuration. The second gas circuit inlet adapter has an inward end and an outward end. The inward end has a first inner diameter. The first inner diameter is mated to the first outer diameter of the gas circuit inlet. In this manner the coupling of the adapter to the gas circuit inlet is allowed. The second gas circuit inlet adapter has an outer end outer diameter. The outer end outer diameter is the same size as the gas circuit inlet outer diameter. The first adapter outlet has an electronic coupling collar 24. The collar is located on the outer diameter of the adapter outlet. The collar is electronically coupled to a second wire.

In an alternative embodiment, the gas circuit outlet and inlet of an anesthesia machine would have a external conductive band 21 about the periphery, that band being coupled to an internal circuit continuity monitor of an anesthesia machine.

An anesthesia breathing circuit subassembly is provided next. The subassembly is fabricated of a flexible material. The subassembly has a pair of tubular circuit breathing hoses. The breathing hoses have a third internal diameter. The breathing hoses have a Y connector and a connecting elbow. Each of the breathing hoses has an outward end and an inward end. A length is provided between the outward and inward ends. The inward end of each hose has an inward coupling end piece 26. The end piece has an outer end 28 and an inner end 30. Each inward end of the end piece has a first internal diameter sized to couple with the first outer diameter of the outer adapter. The end piece of each of the breathing hoses has an electrically conductive collar 32. The collar is within the inner diameter of the inner end piece. In this manner the end piece mates with and forms an electronically conductive connection with the conductive collar of the gas circuit outlet adapter. The end piece collar has an electronically conductive means 31, such as a wire. The electronically conductive means is coupled to the end piece collar. The conductive means passes outwardly within the inner diameter of the length of the breathing hose. Each of the outward ends of the breathing hoses have an outward coupling end piece 36. The outward coupling end piece has an inner end and an outer end 38. The outer end of the outward coupling end piece has a first internal diameter. The inner end of the outward coupling end piece has a third external diameter. Each outer end piece has an electronically conductive means passing from within the length of the breathing hose outwardly through to the outwardmost end of the outward end piece. The inner end of the outward end piece is coupled to the outermost end of the breathing hose.

The Y connector 42 has a generally hollow tubular Y shaped configuration. The Y connector has two inward bifurcated portions 44. The Y connector has an outward common portion 46. Each of the bifurcated portions has a first external diameter and is sized to be accepted into the internal diameter of the outer end of the outward end piece of each of the hoses. The electronically conductive means passes through the internal diameter of the Y connector toward the outward common end. The outward common end of the Y piece has a single hollow tubular configuration. The outward common end of the Y piece has a second internal diameter. The outward common end has a pair of conductive collars 48. The collars are located within the second internal diameter. The collars are circumferentially parallel with a non-conductive space 50 between the collars. Each of the electronically conductive means is coupled to one of the collars in the common end of the Y piece.

The elbow 52 has a generally hollow tubular configuration. The elbow has an inward portion 54 and an outward portion 56. A capnograph connection port 58 is provided between the inward and outward portions. The inward portion has a second external diameter. The outward portion has a second internal diameter. The inward portion has a pair of conductive collars 60. The collars are located on the external surface of the second external diameter. The collars are circumferentially parallel with a non-conductive space 62 between the collars. The second internal diameter of the outward portion of the elbow has a pair of conductive collars 64. The collars are located within the second internal diameter. The collars are circumferentially parallel with a non-conductive space 66 between the collars. A conductive means 34 electronically couples the inward collar of the outward portion and the inward collar of the inward portion. A conductive means electronically couples the outward collar of the outward portion and the outward collar of the inward portion.

Provided next is an endotracheal tube connector 68. The endotracheal tube connector is fabricated of flexible non-conductive material. The endotracheal tube connector has a tubular portion 70 and a coupling portion 72. The coupling portion has a generally hollow tubular configuration. The coupling portion has a second external diameter. The tubular portion has a third external diameter. The external diameter of the coupling portion has a conductive strip 74. The conductive strip is aligned in an inward to outward direction. In this manner the conductive collars of the outward portion of the elbow are electronically coupled when the endotracheal tube connector is pushed into the second internal diameter of the elbow.

Provided last is a capnograph 76. The capnograph has a sampling tube 78. The sampling tube is coupled to the connection port of the elbow. The capnograph also has a pair of wires 80 coupling the capnograph to the circuit adapters. The capnograph also has a program which then initiates an adjustable timer when the endotracheal connector completes the circuit by connecting the collars of the outward elbow with the conductive strip. The timer provides the transmission of an alarm 82 when the circuit had been completed and no carbon dioxide is detected in the breathing hoses within a predetermined amount of time. The program also provides the transmission of a second alarm 84 if carbon dioxide was detected in the anesthesia circuit and the parallel monitoring circuits were not connected by the strip in the endotracheal tube. The second alarm is capable of being turned off. The program also provides a third alarm 86 if the circuit is interrupted once it is connected and made continuous by the endotracheal tube conductive strip.

In an alternate embodiment of the present invention a stand-alone programable circuit monitor 90 is also included. The monitor may be coupled electronically 94 to a capnograph or may be a stand alone circuit monitor 95. The capnograph sends a signal to the stand-alone circuit monitor when the presence of carbon dioxide is detected. The stand-alone circuit monitor determines if alarm criteria is attained and transits an alarm 92 if the criteria is attained.

In the alternative embodiment with a stand-alone monitor, the monitor would not be coupled with the capnograph, but would only monitor circuit continuity.

The present intention also comprises a method for using a disconnect system and thereby allowing a user to monitor continuity within a breathing circuit comprising.

The first step of the method is providing an anesthesia breathing circuit having an electrically conductive coupling between each of the components thereby forming a plurality of unconnected electrical circuits. The anesthesia breathing circuit is coupled electronically to the anesthesia machine having a inlet and an outlet.

The next step is providing an endotracheal tube having a conductive strip thereby allowing a user to connect the unconnected circuits and form a single continuous electrical circuit when the user connects the endotracheal tube to the breathing circuit elbow.

The next step is providing a capnographer having a sampling tube coupled to the breathing circuit, the capnographer also having a pair of wires electrically coupling the capnographer to the electrical circuit, the capnographer also having program which would begin an adjustable timer when the coupling of an endotracheal with the breathing circuit completed the electrical circuit by connecting the collars of the outward elbow with the conductive strip of the endotracheal tube, said timer providing the transmission of an alarm when the circuit had been completed and no carbon dioxide was detected in the breathing hoses within a predetermined amount of time and said timer also providing the transmission of an alarm when the circuit is connected and then disconnected and said timer providing an alarm if carbon dioxide was detected and the electrical circuit was not coupled to a continuous circuit.

The last step is forming a continuous electrical circuit monitoring system which triggers an alarm if the circuit is electrically disconnected and triggers an alarm if the presence of carbon dioxide is not detected within the breathing circuit within a pre-set time and triggers an alarm if carbon dioxide is detected and the electrical circuit is not formed into a continuous circuit, allowing a user to monitor anesthesia circuit continuity and to detect interruptions of the breathing circuit.

An alternative embodiment of the above method would be providing a stand-alone monitor, not coupled with a capnograph, to monitor the continuity of an anesthesia circuit.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A breathing circuit disconnect warning system which allows a user to monitor continuity within a breathing circuit comprising, in combination:

a gas circuit with an outlet having a first outer diameter and an inlet having a first outer diameter;

a first gas circuit outlet adapter having a generally round tubular configuration having an inward end and an outward end, with the inward end having a first inner diameter mated to the first outer diameter of the gas circuit outlet to allow the coupling of the adapter to the gas circuit outlet first outer diameter, and the adapter having an outer end outer diameter to be of the same size as the gas circuit outlet outer diameter, with the first adapter outlet having a first electronic coupling collar located within the inward outer diameter of the adapter outlet with the collar being electronically coupled to a first wire;

a second gas circuit inlet adapter having a generally round tubular configuration having an inward end and an outward end, with the inward end having a first inner diameter mated to the first outer diameter of the gas circuit inlet to allow the coupling of the second adapter to the gas circuit inlet, and the second adapter having an outer end outer diameter to be of the same size as the gas circuit inlet outer diameter, with the second adapter outlet having an electronic coupling collar located within the outward outer diameter of the second adapter outward end with the collar being electronically coupled to a second wire;

an anesthesia breathing circuit subassembly fabricated of a flexible material having a pair of tubular circuit breathing hoses having a third internal diameter and a Y connector and a connecting elbow, each of the breathing hoses having an outward end and an inward end with a length there between, with the inward end having an inward coupling end piece with an outer end and an inner end, with each end piece having an internal diameter of a first inner diameter sized to couple with the first outer diameter of the outlet adapter, the end piece of one of the breathing hoses having an electrically conductive collar within the inner diameter with the collar being located toward an inward end of the inner end of the end piece so as to mate and form an electronically conductive connection with the conductive collar of the first gas circuit outlet adapter, with the end piece collar having an electronically conductive means coupled thereto and the conductive means passing within the length of the other breathing hose outwardly, the end piece of the other breathing hose having an electrically conductive collar within the inner diameter with the collar being located toward an outward end of the inner end of the end piece so as to mate and form an electronically conductive connection with the conductive collar of the second gas circuit outlet adapter, with the end piece collar having an electronically conductive means coupled thereto and the conductive means passing within the length of the other breathing hose outwardly, with each of the outward ends of the breathing hoses having an outward coupling end piece with an outer end having a first internal diameter and an inner end having a third external diameter, with each inner end of the outward coupling end piece having an internal diameter of the first diameter sized to couple with the outer first diameter of the outer adapter and each outward coupling end piece outer end having the third external diameter, the end piece of one of the breathing hoses having an electrically conductive collar within the inner diameter with the collar being located toward the inward end of the inner end of the end piece so as to mate with and form an electronically conductive connection with the conductive collar of the first gas circuit outlet adapter, with the end piece collar having an electronically conductive means coupled thereto and the conductive means passing within the length of the breathing hose outwardly, the end piece of the other breathing hose having an electrically conductive collar within the inner diameter with the collar being located toward the outward end of the inner end of the end piece so as to mate with and form an electronically conductive connection with the conductive collar of the second gas circuit outlet adapter, with the end piece collar having an electronically conductive means coupled thereto and the conductive means passing within the length of the breathing hose outwardly, with each of the breathing hoses also having an outward end piece with the electronically conductive means passing there through outwardly, the Y connector having a generally hollow tubular Y shaped configuration with an inward bifurcated portion and an outward common portion, the bifurcated portion having a first external diameter sized to be accepted into the internal diameter of the outer end of the outward end piece of each of the hoses with the electronically conductive means passing through the internal diameter of the Y connector toward the outward common portion, the outward common portion of the Y connector having a single hollow tubular configuration with a second internal diameter, with the outward common end having a pair of conductive collars located within the second internal diameter, the collars being circumferentially parallel with a non-conductive space between the collars, with each of the electronically conductive means being coupled to one of the collars in the common end of the Y connector, the elbow having a generally hollow tubular configuration with an inward portion and an outward portion and a capnographer connection port there between, the inward portion having a second external diameter and the outward portion having a second internal diameter, with the inward portion having a pair of conductive collars located on the external surface of the second external diameter, the collars being circumferentially parallel with a non-conductive space between the collars, the second internal diameter of the outward portion of the elbow having a pair of conductive collars located within the second internal diameter, the collars being circumferentially parallel with a non-conductive apace between the collars, with a conductive means electronically coupling the inward collar of the outward portion and the inward collar of the inward portion, and a conductive means electronically coupling the outward collar of the outward portion and the outward collar of the inward portion;

an endotracheal tube fabricated of flexible non-conductive material having a tubular portion and a coupling portion, the coupling portion having a generally hollow tubular configuration with a second external diameter and a tubular portion having a third external diameter, the external diameter having a conductive strip aligned in an inward to outward direction so as to electronically couple the conductive collars of the outward portion of the elbow when the endotracheal tube coupling portion was pushed into the second internal diameter of the elbow; and a capnograph having a sampling tube coupled to the connection port of the elbow, the capnograph also having a pair of wires electrically coupling the capnograph to the circuit adapters, the capnograph also having as program which would begin an adjustable timer when the endotracheal coupling portion completed the circuit by connecting the collars of the outward elbow, said timer providing the transmission of an alarm when the circuit had been completed and no carbon dioxide was detected in the breathing hoses within a predetermined amount of time, with the program also providing the transmission of a second alarm if carbon dioxide was detected in the breathing circuit and the parallel monitoring circuits were not connected by the strip in the endotracheal tube, with the second alarm being capable of being turned off and the program also providing a third alarm if the circuit was interrupted once it was connected by the endotracheal tube conductive strip.

2. A breathing circuit disconnect warning system comprising, in combination:

an anesthesia machine gas circuit with an outlet and an inlet each having an electronic coupling collar;

an anesthesia breathing circuit having a pair of tubular breathing circuit hoses and a Y connector and a connecting elbow, the breathing circuit having an electronically conductive system of wires and contacts so as to form two unconnected parallel electric circuits;

an endotracheal tube having a conductive strip aligned so as to electronically couple the separate electric circuits of the breathing circuit; and a capnograph having a sampling tube coupled to the breathing circuit, the capnograph having a program which will provide for the transmission of an alarm.

3. A breathing circuit disconnect warning system as set forth in claim 2 wherein there is also included a stand-alone programable circuit monitor coupled electronically to the capnograph, the capnograph sending a signal to the stand-alone circuit monitor when the presence of carbon dioxide is detected with the stand-alone circuit monitor determining if alarm criteria is attained.

4. A breathing circuit disconnect warning system as set forth in claim 2 wherein there is also included a stand-alone programable circuit monitor, the monitor providing an alarm signal if breathing circuit electronic continuity is interrupted.

5. A breathing circuit disconnect warning system comprising, in combination:

an anesthesia machine gas circuit with an outlet;

a plurality of breathing circuit adapters, with each adapter having an electronic coupling collar, the collar being coupled to a wire;

an anesthesia breathing circuit having a pair of tubular breathing circuit hoses and a Y connector and a connecting elbow, the breathing circuit having electronically conductive wires and contacts so as to form two unconnected parallel electric circuits;

an endotracheal tube having a conductive strip aligned so as to electronically couple the separate electric circuits of the breathing circuit; and a capnograph having a sampling tube coupled to the breathing circuit, the capnograph also electrically coupled to the separate electric circuits in the breathing circuit, the capnograph also having a program which would begin an adjustable timer when the endotracheal tube conductive strip completed the electrical circuit by connecting the endotracheal tube to the breathing circuit, said timer providing for the transmission of an alarm when the circuit had been completed and no carbon dioxide was detected in the breathing hoses within a predetermined amount of time, the timer ales providing for the transmission of an alarm when the circuit had been completed and had been disconnected thereafter.

6. A breathing circuit disconnect warning system as set forth in claim 5 wherein the wires run along the exterior of the anesthesia breathing circuit.

7. A breathing circuit disconnect warning system as set forth in claim 5 wherein the wires conduct an induction signal to determine breathing circuit continuity.

8. A method for using a disconnect system and thereby allowing a user to monitor continuity within a breathing circuit comprising, in combination:

providing an anesthesia breathing circuit having an electrically conductive coupling positionable within the circuit thereby forming a plurality of dis connectable electrical circuits;

providing an endotracheal tube having a conductive strip thereby allowing a user to connect the disconnectable circuits and form a single continuous electrical circuit when the user connects the endotracheal tube to a breathing circuit outboard elbow with a collar; and providing an electrical circuit continuity monitor to alarm if the electrical continuity of the breathing circuit is interrupted;

thereby forming a continuous electrical circuit monitoring system which triggers an alarm if the circuit is electrically disconnected.

9. A method for using a disconnect system as described in claim 8 wherein the method further comprises:

providing a capnographer having a sampling tube coupled to the breathing circuit, the capnographer also having a pair of wires electrically coupling the capnographer to the electrical circuit, the capnographer also having a program which would begin an adjustable timer when the coupling of the endotracheal tube with the breathing circuit completed the electrical circuit by connecting the collar of the outward elbow with the conductive strip of the endotracheal tube, said timer providing the transmission of an alarm when the circuit had been completed and no carbon dioxide was detected in the breathing circuit within a predetermined amount of time and said timer also providing the transmission of an alarm when the circuit is connected and then disconnected and said timer providing an alarm if carbon dioxide was detected and the electrical circuit was not coupled to a continuous circuit;

thereby forming a continuous electrical circuit monitoring system which triggers an alarm if the circuit is electrically disconnected and triggers an alarm if the presence of carbon dioxide is not detected within the breathing circuit within a pre-set time and triggers an alarm if carbon dioxide is detected and the electrical circuit is not formed into a continuous circuit, allowing a user to monitor anesthesia circuit continuity and to detect interruptions of the breathing circuit.

* * * * *